(12) United States Patent
Hoang

(10) Patent No.: US 7,301,158 B1
(45) Date of Patent: Nov. 27, 2007

(54) METHOD AND APPARATUS FOR MEASURING ACTIVE FLUORESCENCE

(75) Inventor: Sang Hoang, Campbell, CA (US)

(73) Assignee: Turner Designs, Inc., Sunnyvale, CA (US)

( * ) Notice: Subject to any disclaimer, the term of this patent is extended or adjusted under 35 U.S.C. 154(b) by 0 days.

(21) Appl. No.: 11/303,446

(22) Filed: Dec. 15, 2005

Related U.S. Application Data

(60) Provisional application No. 60/637,478, filed on Dec. 15, 2004.

(51) Int. Cl.
*G01N 21/49* (2006.01)

(52) U.S. Cl. .................... 250/458.1; 250/573

(58) Field of Classification Search ............. 250/458.1, 250/573
See application file for complete search history.

(56) References Cited

U.S. PATENT DOCUMENTS

| | | | |
|---|---|---|---|
| 4,650,336 A | | 3/1987 | Moll |
| 4,652,143 A | * | 3/1987 | Wickersheim et al. ...... 374/161 |
| 4,750,837 A | * | 6/1988 | Gifford et al. ............. 356/417 |
| 4,802,768 A | * | 2/1989 | Gifford et al. ............. 356/417 |
| 4,804,850 A | * | 2/1989 | Norrish et al. ........... 250/459.1 |
| 4,942,303 A | * | 7/1990 | Kolber et al. ............ 250/458.1 |
| 5,350,922 A | | 9/1994 | Bartz |
| 5,418,614 A | | 5/1995 | Brost et al. |
| 5,424,840 A | * | 6/1995 | Moore et al. ................ 356/410 |
| 5,426,306 A | | 6/1995 | Kolber et al. |
| 6,121,053 A | | 9/2000 | Kolber et al. |
| 6,255,118 B1 | | 7/2001 | Alfano et al. |
| 6,307,630 B1 | | 10/2001 | Banerjee |
| 6,369,894 B1 | | 4/2002 | Rasimas et al. |
| 6,563,122 B1 | * | 5/2003 | Ludeker et al. .......... 250/458.1 |
| 6,836,325 B2 | | 12/2004 | Maczura et al. |
| 7,099,012 B1 | | 8/2006 | Crawford et al. |
| 2004/0179196 A1 | * | 9/2004 | Hart ........................... 356/318 |

\* cited by examiner

*Primary Examiner*—David Porta
*Assistant Examiner*—Mark R Gaworecki
(74) *Attorney, Agent, or Firm*—Adeli Law Group, PLC

(57) ABSTRACT

Some embodiments of the invention provide an apparatus for measuring active fluorescence in liquid samples by using solid-state components. The use of solid-state devices dramatically lowers the cost, size, and power consumption of active fluorescence while improving the ruggedness and reliability. The smaller size of the solid-state devices allows them to be placed very close to the sample. This maximizes the amount of light the sample receives from the light sources and allows efficient collection of the resulting emitted light using simple and low cost optical components.

22 Claims, 12 Drawing Sheets

Top View

Top View

Top View

Side View

Top View

Side View

METHOD AND APPARATUS FOR MEASURING ACTIVE FLUORESCENCE

CLAIM OF BENEFIT TO PROVISIONAL APPLICATION

This Application claims priority to U.S. Provisional Patent Application 60/637,478, entitled "Method and Apparatus for measuring active fluorescence", filed Dec. 15, 2004. This provisional application is incorporated herein by reference.

BACKGROUND OF THE INVENTION

The use of fluorescence to measure the photosynthetic activity of organisms has been an accepted method in the scientific community for many years. Measuring fluorescence as a function of photosynthetic activity, compared to other methodologies, is fast, easy to use, and requires relatively low cost instrumentation. The majority of fluorometers in use today are classified as passive fluorometers and are used to measure the total biomass of photosynthetic organisms. Passive fluorometers supply a constant source of light of a specific wavelength and measure the light output from the sample at a different, typically longer, wavelength. In order to measure sample levels as low as possible, passive fluorometers typically use as bright a light as possible.

A known drawback to using passive fluorescence is that the fluorescent output of a sample can vary due to several influences not related to biomass of the photosynthetic organisms. For example, an organism's fluorescent light output will vary depending on the ambient light condition of its environment. In addition, the source light used by the fluorometer can affect the organism being measured.

Active fluorescence overcomes these issues by using flash stimulated fluorescence. An example of active fluorescence is disclosed in Moll, U.S. Pat. No. 4,650,336. Moll describes a method and device to measure photosynthetic activity using variable fluorescence. Moll uses one lamp to provide constant-level light to bring about continuous, steady state fluorescence of a plant, and a flash lamp to provide a flash of light to bring about a transient fluorescence of the plant.

Another active fluorescence technique is described in Kolber et al., U.S. Pat. No. 4,942,303 ("Kolber I"). Kolber I describes a "pump and probe" technique that uses a low intensity "probe" flash to measure fluorescence before and after a bright "pump" flash to measure the change in fluorescence.

Another active fluorescence technique is described in Kolber et al., U.S. Pat. No. 5,426,306 ("Kolber II"). This technique, known as fast repetition fluorescence, uses a series of fast, repetitive flashes at controlled energies to incrementally effect photosynthetic processes.

Another active fluorescence technique is described in Kolber et al., U.S. Pat. No. 6,121,053 ("Kolber III"). Kolber III describes a multiple protocol fluorometer which allows a significant amount of control over the duration, frequency, and power of the flashes.

The trend in active fluorometer development, as can be seen in the references, has been towards providing researchers with progressively more control over the active fluorescence protocol with the goal of providing increasingly detailed information of the photosynthetic process. While this is a laudable goal, it has led to the development of increasingly complex and costly instruments. With limited research budgets, many researchers cannot afford the instruments currently available.

The components used by current active fluorometers are one reason for their high costs. Bright light sources such as the flash lamps used in Kolber I and Kolber II require a large amount of energy to work properly, and require expensive support circuitry to supply the currents they need. Moving to solid state LEDs as used in Kolber III is a step in the right direction, since they require less power and less support circuitry. But Kolber III uses a large array of LEDs driven above their nominal currents, again requiring a significant amount of energy. The use of bright light sources is due to the weak fluorescent response of algae in water as compared to solid samples (e.g., a leaf). Using a bright light helps maximize the response to improve detection limits.

Another source of large material cost is the detector for measuring the light emitted by the sample. Because the emitted light is relatively dim for algae in water, the photodetector in the above references has been a photomultiplier tube ("PMT"). A PMT is a vacuum tube with special elements to convert a detected photon to an electrical current which is then amplified internally before being provided to outside circuitry for further signal processing. PMTs are inherently expensive due to their specialized nature, many are built by hand. In addition, they require high voltage sources to operate (e.g., up to 1000 volts) which can also be expensive. Due to their construction, PMTs are fairly fragile. Not only are they encased in glass under vacuum, but the internal elements are small metal plates that are carefully aligned. PMTs therefore do not handle shock very well. In addition, PMTs are typically physically large. This makes it difficult to place them near the sample. Kolber II uses optics such as lenses and collimators to collect emission light from the sample and provide it to the PMT, again increasing components, complexity, and cost.

Further costs have been added due to the emphasis on increasing control, data acquisition, and data analysis to calculate the many parameters of photosynthesis. This requires the use of more powerful, and hence more costly, internal computers.

The light sources, detectors, and computers of the current designs are all large and require a significant amount of power. This leads to large enclosures and large power sources, again increasing costs.

In addition to limited or decreasing budgets, there is a trend among researchers towards the deployment of multiple sensors in situ in various locations collecting data in real time to give a broader view of the health of a body of water. Often these instruments are deployed in fixed locations (e.g., a pier) and are left unattended to operate for significant periods of time (e.g., one month). An ideal instrument would have a low enough cost to allow the purchase of multiple units and would have low enough power consumption to operate on a battery for the necessary period of time. In addition, many studies only require the information that can be provided by a basic active fluorometer. All of these factors lead to the conclusion that there is a need for a small, low cost, low power, and reliable active fluorometer.

SUMMARY OF THE INVENTION

Some embodiments of the invention provide an apparatus for measuring active fluorescence in liquid samples by using solid-state components. The use of solid-state devices dramatically lowers the cost, size, and power consumption of active fluorescence while improving the ruggedness and reliability. The smaller size of the solid-state devices allows them to be placed very close to the sample. This maximizes the amount of light the sample receives from the light sources and allows efficient collection of the resulting emitted light using simple and low cost optical components.

In some embodiments, the apparatus (1) uses either a single LED or a few LEDs (4 or fewer) that are modulated to provide a measuring light source and (2) uses a small number of LEDs (12 or fewer) to provide a saturating light source. Also, the apparatus includes a photodetector that is a photodiode. The apparatus includes amplification circuitry associated with this photodiode. This amplification circuitry is synchronized to both the modulating light source and the analog to digital conversion. The apparatus in some embodiments further includes a small, low power microcontroller to control the light sources and to read, report, and/or record the output from the photodiode and its associated circuitry.

BRIEF DESCRIPTION OF THE DRAWINGS

The novel features of the invention are set forth in the appended claims. However, for purpose of explanation, several embodiments of the invention are set forth in the following figures.

DETAILED DESCRIPTION OF THE INVENTION

In the following description, numerous details are set forth for purpose of explanation. However, one of ordinary skill in the art will realize that the invention may be practiced without the use of these specific details. In other instances, well-known structures and devices are shown in block diagram form in order not to obscure the description of the invention with the unnecessary detail.

I. Active Fluorometer

Figure 1:
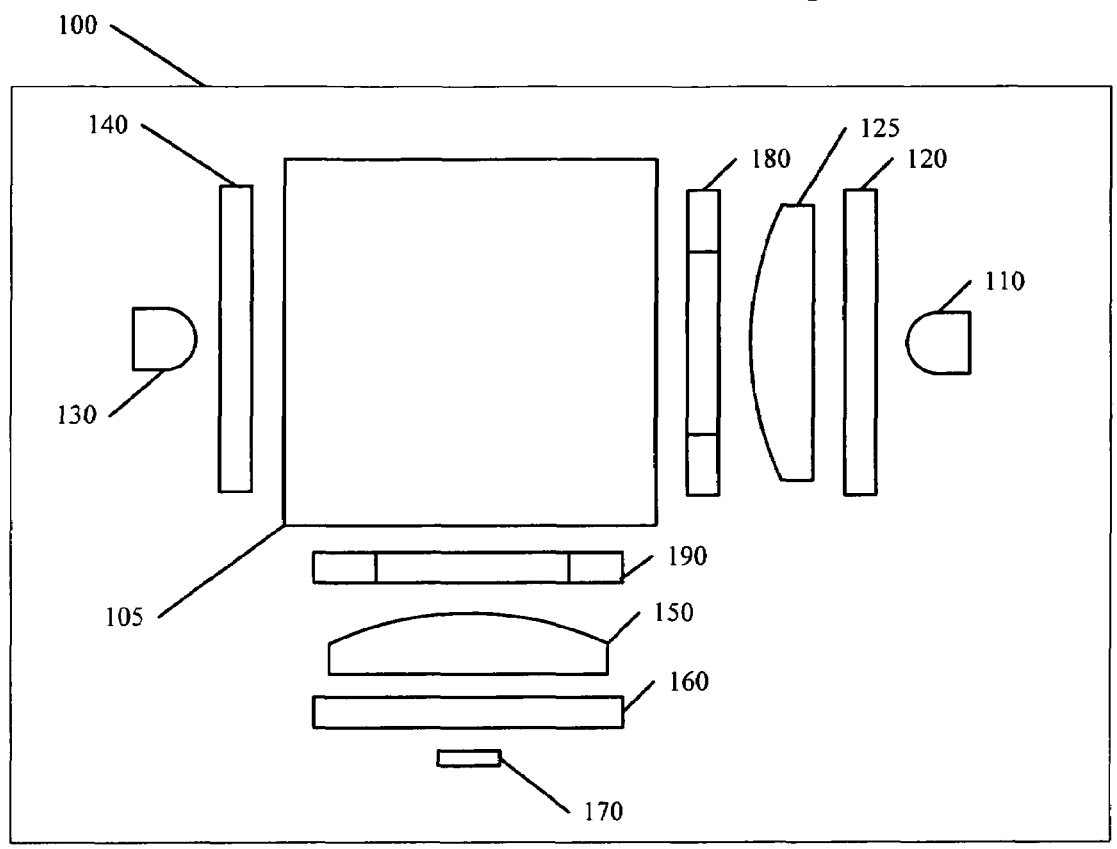
FIG. 1 illustrates a top view of the components of the fluorometer.

FIG. 1 conceptually illustrates a fluorometer having an optical configuration 100. As shown in this figure, the optical configuration 100 includes a sample container 105, a sampling light emitting diode ("LED") 110, an excitation filter 120, a first optical lens 125, a saturating LED 130, a saturation excitation filter 140, a second optical lens 150, an emission filter 160, a photodiode 170, a first aperture 180 and a second aperture 190.

In some embodiments, a water sample can be placed in the sample container 105. While FIG. 1 illustrates the sample container 105 to be square, in other embodiments, the sample container 105 can just as easily be round, rectangular, or other shapes depending on physical requirements.

The sampling LED 110 is oriented to shine into the sample water. Specifically, during the operation of the fluorometer, the sampling LED is modulated to provide a measuring light source. FIG. 1 illustrates one sampling LED 110. However, in other embodiments, there can be more than one sampling LED 170.

In some embodiments, the excitation filter 120 is placed between the sampling LED 110 and the sample container 105. Some embodiments that have more than one sampling LED have one excitation filter for each sampling LED. Other such embodiments might share one excitation filter among more than one sampling LED. While the LEDs in general produce a narrow bandwidth of light, adding the excitation filter 120 further reduces the bandwidth to the wavelength of interest and generally produces more satisfactory results. In other words, the excitation filter filters out wavelengths of light (emitted by the LED or LEDs) that are not of interest (i.e., that do not lead to the desired fluorescence effect).

In some embodiments, the lens 125 is placed between the sampling LED excitation filter 120 and the sample container 105 to focus the light from the sampling LED 110. The aperture 180 collimates the light from the sampling LED 110 and helps to prevent stray light from shining directly into the photodiode 170.

At least one saturating LED 130 is placed around the sample, with one or more excitation filter(s) 140. During the operation of the fluorometer, the saturating LED 130 provides a saturating light source, while its associated excitation filter 140 filters out wavelengths of light (emitted by its LED) that are not of interest (i.e., that do not lead to the desired saturation effect). The embodiments that use multiple saturation LEDs might share one excitation filter among more than one saturation LED.

The saturating LED 130 is typically the same type of LED as the sampling LED 110, though the saturating LED 130 may be driven at higher currents to give maximum light output. In some embodiments, the excitation filter 140, if used, is typically the same type of filter as the excitation filter 120. FIG. 1 only shows one saturating LED 130, however there can be as many as needed to fully saturate the water sample. In some embodiments, with a small sample volume, typically 12 or fewer saturating LEDs 130 and their associated excitation filters 140 are needed. A saturating LED 130 may be oriented in any direction, though it is usually advisable to avoid shining the LED directly at the photodiode 170.

In some embodiments, the detector is the photodiode 170 that is typically oriented orthogonally to the sampling LED 110. The photodiode 170 has an emission filter 160 to measure only the wavelength of interest. The lens 150 is optionally used in some embodiments to gather more light from the sample and focus the light on the photodiode 170. The aperture 190 is again used to collimate the emission light and to prevent stray light from sampling LED 110 or saturating LED 130 from reaching the photodiode 170.

The saturation operation of some embodiments provides light to the sample for a long enough period of time to cause the sample to be at its maximum fluorescence.

When the sampling LED 110 is on, it causes some living things in the water to fluoresce, but when the sampling LED is off, the photodiode 170 may still receive some light, either ambient light, or light from the saturating LED 130, or fluorescence caused by the saturating LED 130. The fluorometer distinguishes between fluorescence caused by these extraneous sources by measuring the light received by photodiode 170 when sampling LED 110 is on, and when it is off. The difference between these two measurements is the relative fluorescence of the sample.

As further described by reference to FIG. 5 below, the system in some embodiments initially takes a measurement using just the sampling LED. This measurement defines the Fo level, and can be used for comparison to later measurements. The system then turns on the saturating LED 130 for some longer period of time, in order to cause the sample to reach its maximum fluorescence Fm, which the system measures using the sampling LED. The system then uses the measured Fo and Fm levels to measure the sample's yield, which is indicative of the health of the living things in the sample.

II. Circuitry for Active Fluorometer

Figure 2:
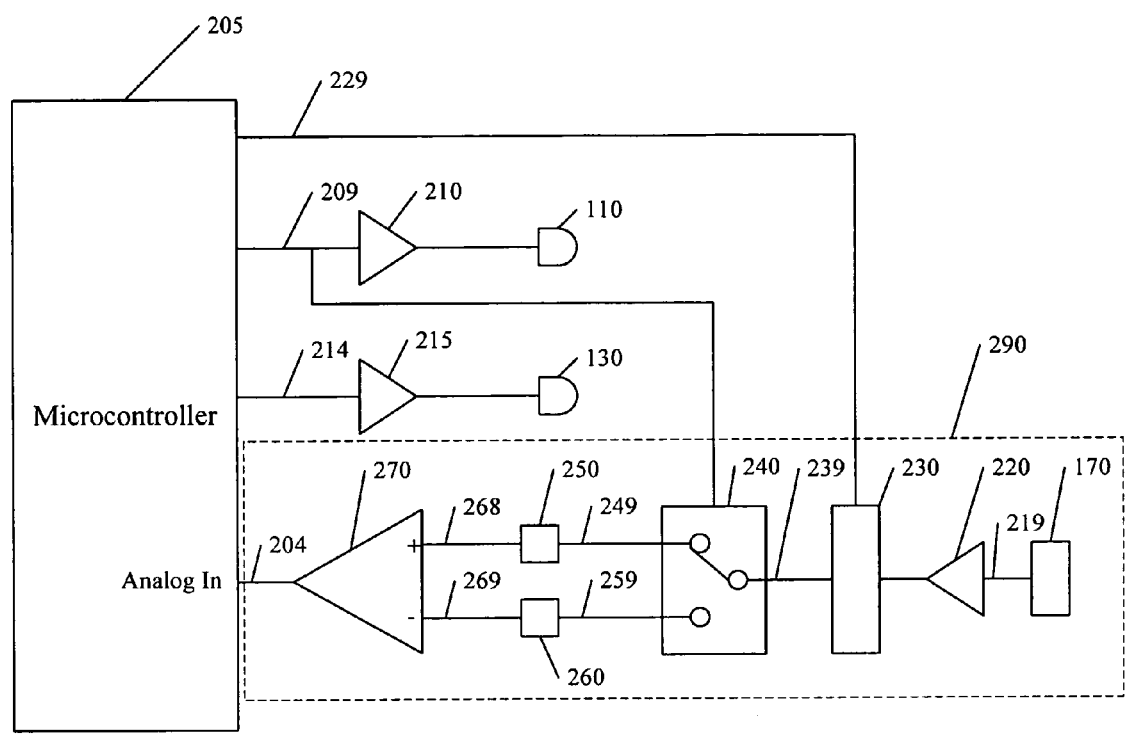
FIG. 2 illustrates a block diagram of the electronic components of the fluorometer

FIG. 2 conceptually illustrates the electronic control system 200 of the fluorometer of some embodiments. This control system includes a microcontroller 205, a sampling LED drive circuit 210, a saturation LED drive circuit 215, an amplifier 220, a gain control circuit 230, an analog switch 240, a first hold circuit 250, a second hold circuit 260, and a differential amplifier 270 and a detection circuit 290.

The microcontroller 205 for driving the sampling LED 110 and saturating LED 130, and processing signals from the photodiode 170. In some embodiments, the microcontroller 205 is a commercially available low cost microcontroller that includes a processor, a memory, digital inputs and outputs, an analog to digital converter, and a communicator for communicating with an external computer. While there are many low cost commercially available microcontrollers, some embodiments may use a dedicated microcontroller that is specifically designed for the fluorometer.

The microcontroller 205 is responsible for supplying signals that determine (1) when the sampling LED 110 turns on and off, (2) when the saturating LED 130 turn on and off, (3) what gain should be selected by the gain control circuit 230, etc. The gain control circuit 230 will be further described below. A digital signal 209 from the microcontroller 205 controls the sampling LED drive circuit 210. Similarly, a digital signal 214 from the microcontroller 205 controls the saturating LED drive circuit 215. The LED drive circuits 210 and 215 are designed to supply a precise amount of current to the sampling LED 110 and saturating LED 130 respectively, and to turn on and off the sampling LED 110 and saturating LED 130 very quickly.

In some embodiments, detection circuit 290 (illustrated in more detail in FIG. 3) includes the photodiode 170 that supplies a small signal 219 to the amplifier 220 which boosts the small signal 219 to a larger value. The output of the amplifier 220 goes to the gain control circuit 230. The gain control circuit 230 is controlled by a digital signal 229 from the microcontroller 205. The purpose of gain control circuit 230 is to further amplify the output of the amplifier 220 if needed so that the signal is at a level which can be read by the analog input of the microcontroller 205. If the output signal of the amplifier 220 is small, then additional gain would be selected. If the output signal of the amplifier 220 is large, then no additional gain would be needed.

The output signal 239 from the gain control circuit 230 goes to the analog switch 240. The analog switch 240 is controlled by the same signal 209 which drives the sampling LED circuit 210. By switching in this manner, the output signal 249 of the analog switch 240 will always present the signal from the photodiode 170 when the sampling LED 110 is on. Likewise, the output signal 259 of the analog switch 240 will always present the signal from the photodiode 170 when the sample LED 110 is off. The hold circuits 250 and 260 are needed to hold the signal levels of the output signals 249 and 259 respectively, since the output signals 249 and 259 are not constantly present due to the continuous switching of the analog switch 240. The hold circuit 250 will hold the amplified signal from the photodiode 170 when the sampling LED 110 is on. The hold circuit 260 will hold the amplified signal from the photodiode 170 when the sampling LED 110 is off.

The output signal 268 of the hold circuit 250 becomes the signal to the positive input of the differential amplifier 270. The output signal 269 of the hold circuit 250 becomes the signal to the negative input of the differential amplifier 270. The output signal 204 of the differential amplifier 270 is the amplified difference between the output signals 268 and 269.

As mentioned above in the description of FIG. 1, the fluorometer of these embodiments measures the effect of the sampling LED 110 by subtracting out the level of light found when the sampling LED 110 is off. In some embodiments, the differential amplifier 270 is used to perform ambient light rejection. Ambient light is light in the sample's environment that is not a function of fluorescence. As such, it is an unwanted background signal. By measuring the output of the photodiode 170 when the sampling LED 110 is off, the ambient light is determined and subtracted from the measured light when the sampling LED 110 is on, thus providing a measure of fluorescence which is not affected by background illumination (e.g., ambient light). In some embodiments, where measurements are taken while the saturating LED 130 is turned on, the differential amplifier also serves to reject that portion of the fluorescence that is caused by the saturating LED 130 and not by the sampling LED 110. An analog to digital circuitry contained in the microcontroller 205 uses the output signal 204 from the differential amplifier 270 and converts it to a digital value which is then communicated externally. In some embodiments, the microcontroller 205 takes multiple samples during each cycle of the output signal 204 and averages them to reduce signal noise. The end result is a produced digital value that is more accurate.

In some embodiments, some functions (e.g., analog to digital converter) of the microcontroller 205 could be incorporated as a separate circuit. Furthermore, in some embodiments, some circuits (e.g., differential amplifier 270) described could also be incorporated in the microcontroller 205. Where some of the circuits are incorporated in the control system 200 is simply a design choice involving cost, size, accuracy and other factors typical in electrical system design.

Figure 3:
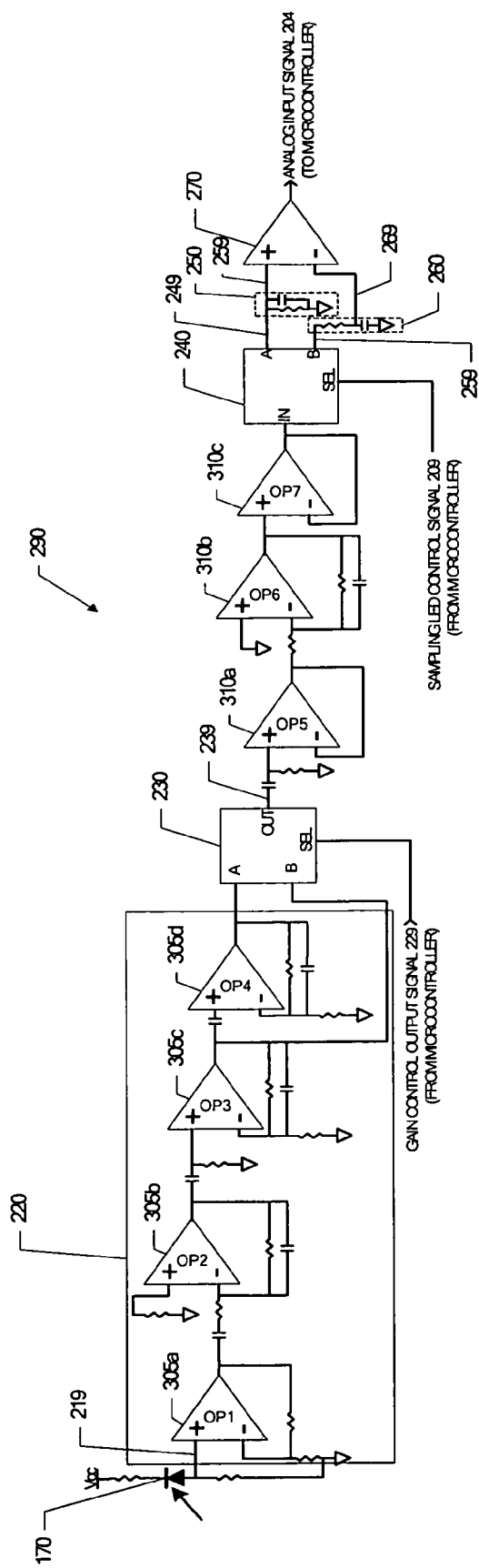
FIG. 3 illustrates a schematic of the detection circuit of the fluorometer.

FIG. 3 describes in more detail the detection circuitry 290 of some embodiments of the invention. The detection circuitry includes, photodiode 170, operational amplifiers 305a-305d (collectively operational amplifiers 305) and 310a-310c (collectively operational amplifiers 310), gain control circuit 230, gain control output signal 229, output signal 239, analog switch 240, sampling LED control signal 209, output signal 249, "on" hold circuit 250, "off" hold circuit 260, output signal 259, differential amplifier 270, output signal 269, analog input signal 204 and several resistors and capacitors, whose values are selected to provide the desired gains for the particular operational amplifiers.

Photodiode 170 supplies a small signal to the input of operational amplifier 305a. Operational amplifiers 305a through 305d (collectively operational amplifiers 305) and their associated resistors and capacitors form amplifier 220 to provide the amplification necessary to detect the signal. Operational amplifier 305a converts the current output of photodiode 170 to a voltage. Operational amplifiers 305b through 305d each provide amplification of the signal using their associated resistors while simultaneously providing some filtering of unwanted noise using their associated capacitors. This use of cascading amplification and filtering provides a much cleaner signal than a single, larger amplifier.

The output of amplifier 220 feeds into gain control circuit 230. Gain control circuit 230 can select between two levels of amplification provided by amplifier 220. The selection of the level of amplification is done by the microcontroller using gain control output signal 229. Note that there could be more than two levels of amplification selection if needed.

Output signal 239 from gain control circuit 230 goes through operational amplifiers 310a through 310c (collectively operational amplifiers 310). Operational amplifiers 310a through 310c buffer the signal between gain control circuit 230 and analog switch 240 while simultaneously filtering out noise that may have been introduced by gain control circuit 230.

Analog switch 240 is controlled by sampling LED control signal 209 provided by the microcontroller. Sampling LED control signal 209 also controls the flashing of sampling LED circuit 210 (not shown in this figure). Analog switch 240 will select one of two possible output signals. Output signal 249 will be selected when sampling LED 110 is on, output signal 259 will be selected when sampling LED 110 is off.

A resistor and capacitor network form the "on" hold circuit 250 for the signal when sampling LED 110 is on. Similarly, a resistor and capacitor network form the "off" hold circuit 260 for the signal when sampling LED 110 is off. The output signal 259 of the "on" hold circuit 250 is connected to the positive input of differential amplifier 270. The output signal 269 of the "off" hold circuit 260 is connected to the negative input of differential amplifier 270. Resulting analog input signal 204 is a signal that is proportional to the fluorescence of the sample.

III. Timing of Circuitry

Figure 4:
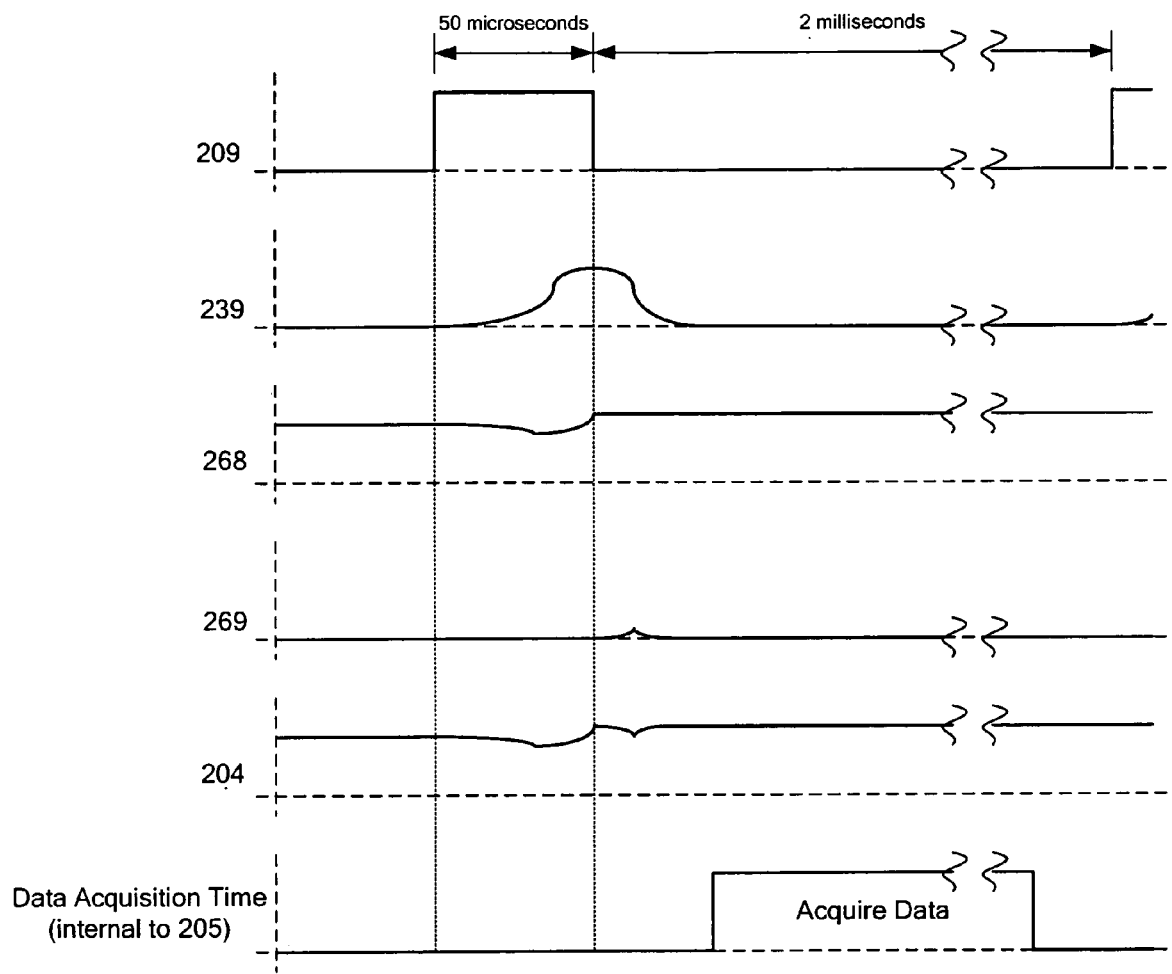
FIG. 4 illustrates a graph of the timing of the sampling LED and the measuring electronic components.

FIG. 4 illustrates a timing diagram of the detection circuit 290 in some embodiment of the invention. In an active fluorescent circuit, the sampling LED 110 ideally should not affect the sample. In other words, turning on the sampling LED 110 should not change the steady state fluorescence of the sample. In order to achieve this, the sampling LED 110 should be on for as little time as possible while still allowing the detection circuit enough time to distinguish the fluorescent signal. Thus, the sampling LED control signal 209 has a very short "on" time for the sampling LED 110.

As shown in FIG. 4, the sampling LED control signal 209 is on for 50 microseconds and off for 2 milliseconds, in some embodiments. However, other embodiments have on and off times that may vary according to various conditions. As illustrated in FIG. 4, the "on" time typically is significantly shorter than the "off" time.

In some embodiments, the gain control output signal 239 is an analog signal showing the detection of the fluorescent signal by the photodiode 170 above the ambient light. As shown in FIG. 4, the gain control output signal 239 will start to rise as the sampling LED 110 is turned on by the sampling LED control signal 209 and reaches its maximum before the sampling LED 110 is turned off. As further shown in this figure, the gain control output signal 239 returns to the ambient light reading when the sampling LED control signal 209 turns the sampling LED 110 off.

In some embodiments, the gain control output signal 239 is the input signal to the analog switch 240. The analog switch 240 is switched using the same sampling LED control signal 209 that controls the sampling LED 110. This means that the output signal 249 of analog switch 240 will only see the gain control output signal 239 when the sampling LED 110 is on. Likewise the output signal 259 of the analog switch 240 will only see the gain control output signal 239 when the sampling LED 110 is off. As mentioned above, these signal levels will be held by the hold circuits 250 and 260 respectively. As shown in FIG. 4, the "on" hold output signal 268 is a signal that is higher than the "off" hold output signal 269. Both the hold output signals 269 and 269 are very slow varying signals (i.e., they will not change significantly from cycle to cycle).

As previously described, the "on" hold output signal 268 becomes the positive input signal to the differential amplifier 270, while the "off" hold output signal 269 becomes the negative input signal. The differential amplifier 270 outputs the analog input signal 204, which is proportional to the difference between the hold output signals 268 and 269. In some embodiments, the microcontroller 205 will start sampling the analog input signal 204 about 100 microseconds after the sampling LED control signal 209 turns the sampling LED 110 off. In some embodiments, the microcontroller 205 may take multiple samples and averages them to obtain a value for the fluorescent signal. However, the averaging will be completed before the sampling LED control signal 209 turns the sampling LED 110 on for the next cycle.

One useful feature of some embodiments is that the sample LED 110 and the detection circuitry can remain synchronized by using the same control signal. In the general use of the fluorometer, the sampling LED 110 sends a signal (the light) into the sample, and the sample's response to that light is measured. It is useful if the detection circuitry is set up so that it detects when the response is actually happening. So in some embodiments, the design circuitry uses only one signal, namely the sampling LED control signal 209, to control both the sampling LED 110 and the detection circuitry 290. With only one signal turning on both the sampling LED 110 and the detection circuitry 290 the whole system remains synchronized, which enhances the accuracy of the measurement. In alternate embodiments which use separate signals control the LED 110 and the analog switch 240, small differences in timing lead to significant measurement errors.

IV. Method for Measuring Photosynthesis Parameters

Figure 5:
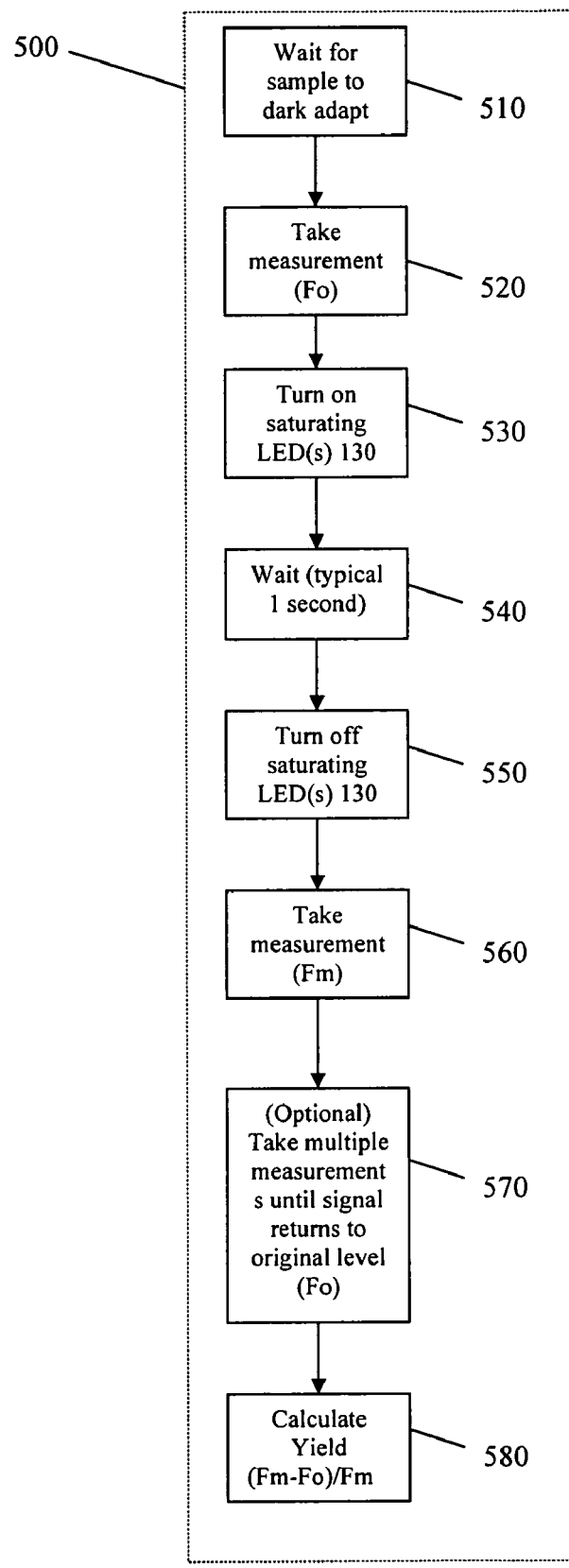
FIG. 5 illustrates a flow chart of the process to obtain information on the photosynthetic process.

FIG. 5 conceptually illustrates a typical process 500 performed by the microcontroller 205 to gather information on a photosynthetic process. This process is generally performed on a sample of water in which photosynthetic material is potentially present. Often this material would be some form of plant life, or other photosynthetic life, or bits of such life. As shown in this figure, the process begins by waiting (at 510) for a sample to "dark adapt". During this step, the sample is left in the dark for a period of time (anywhere from a few seconds to 10 minutes) so that very little photosynthesis is taking place. This causes the sample to fully utilize any light available for photosynthesis when it becomes available, which also gives a minimum fluorescent signal ("Fo").

In some embodiments, once the sample is dark adapted (at 510), the process takes (at 520) a measurement or series of measurements of the Fo, using the sampling LED 110 to illuminate the sample, to obtain a minimum fluorescent value. The illumination by the sampling LED 110 causes the sample to fluoresce, the detection circuitry 290 then detects this fluorescence. After obtaining (at 520) the minimum fluorescent value, the process turns on (at 530) the set of one or more saturating LEDs 130. The process leaves (at 540) the set of LEDs 130 on for some period of time. In some embodiments, the process leaves the set of LEDs 130 on for one second. In other embodiments, the process leaves the one or more saturating LED 130 for a varying amount of time. Some embodiments allow a user to select the period of time for leaving "on" the saturating LED.

After leaving the one or more saturating LED(s) 130 for a period of time, the process turns off (at 550) the one or more saturating LED(s) 130. In some embodiments, the process takes (at 560) a measurement of a maximum fluorescent signal (Fm), using the sampling LED 110 to illuminate the sample, to obtain a maximum fluorescent value. The illumination by the sampling LED 110 causes the sample to fluoresce, the detection circuitry 290 then detects this fluorescence. This measurement is made as quickly as possible after turning off (at 550) the one or more saturating LED 130. After taking (at 560) the Fm, the process continues to take (at 570) additional measurements of the fluorescent signal generated by the sample, using the sampling LED 110 to illuminate the sample. The illumination by the sampling LED 110 causes the sample to fluoresce, the detection circuitry 290 then detects this fluorescence. These measurements continue until the fluorescent signal returns to the Fo level, in some embodiments. Some embodiments use these additional measurements to determine other parameters of the photosynthetic process. Once the process measures the Fm, the process determines (at 580) a yield for the sample. The yield is defined as the difference between Fm and Fo divided by Fm. The yield is a measurement of the health of the living things in the water, a high yield indicates they are healthy, a low yield indicates they are unhealthy.

In some embodiments of the invention, measurements are taken using the sampling LED while the saturating LED is still on at 540. In such embodiments the photodiode 170 has a high enough dynamic range to distinguish between fluorescence caused by the sampling LED 110 and fluorescence caused by the saturating LED 130. In some such embodiments, the maximum measurement of the fluorescence taken at 540 is used as the Fm, rather than the value measured at 560.

Figure 6:
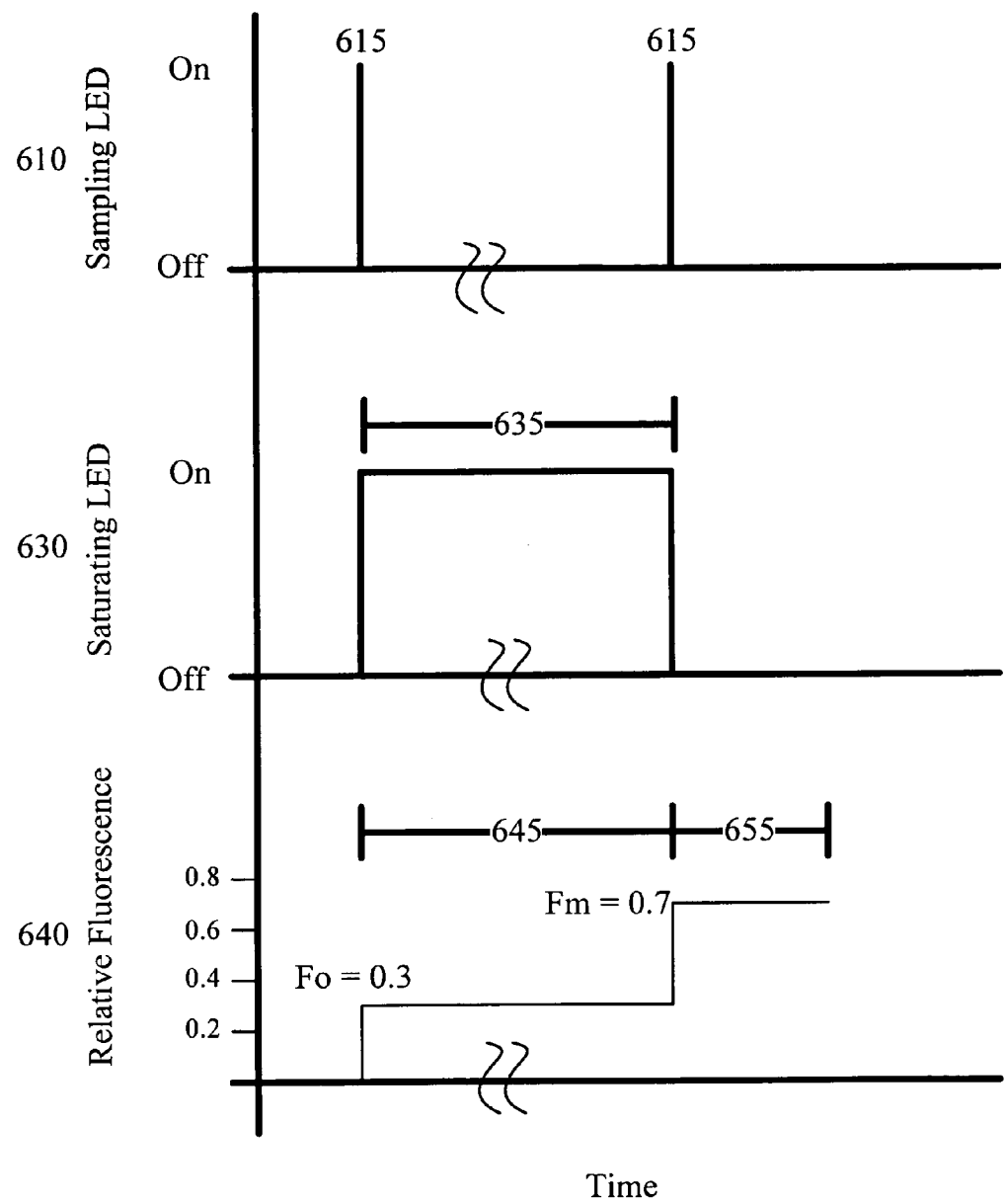
FIG. 6 illustrates a protocol for the fluorometer to determine certain parameters of the photosynthetic process.
Figure 7:
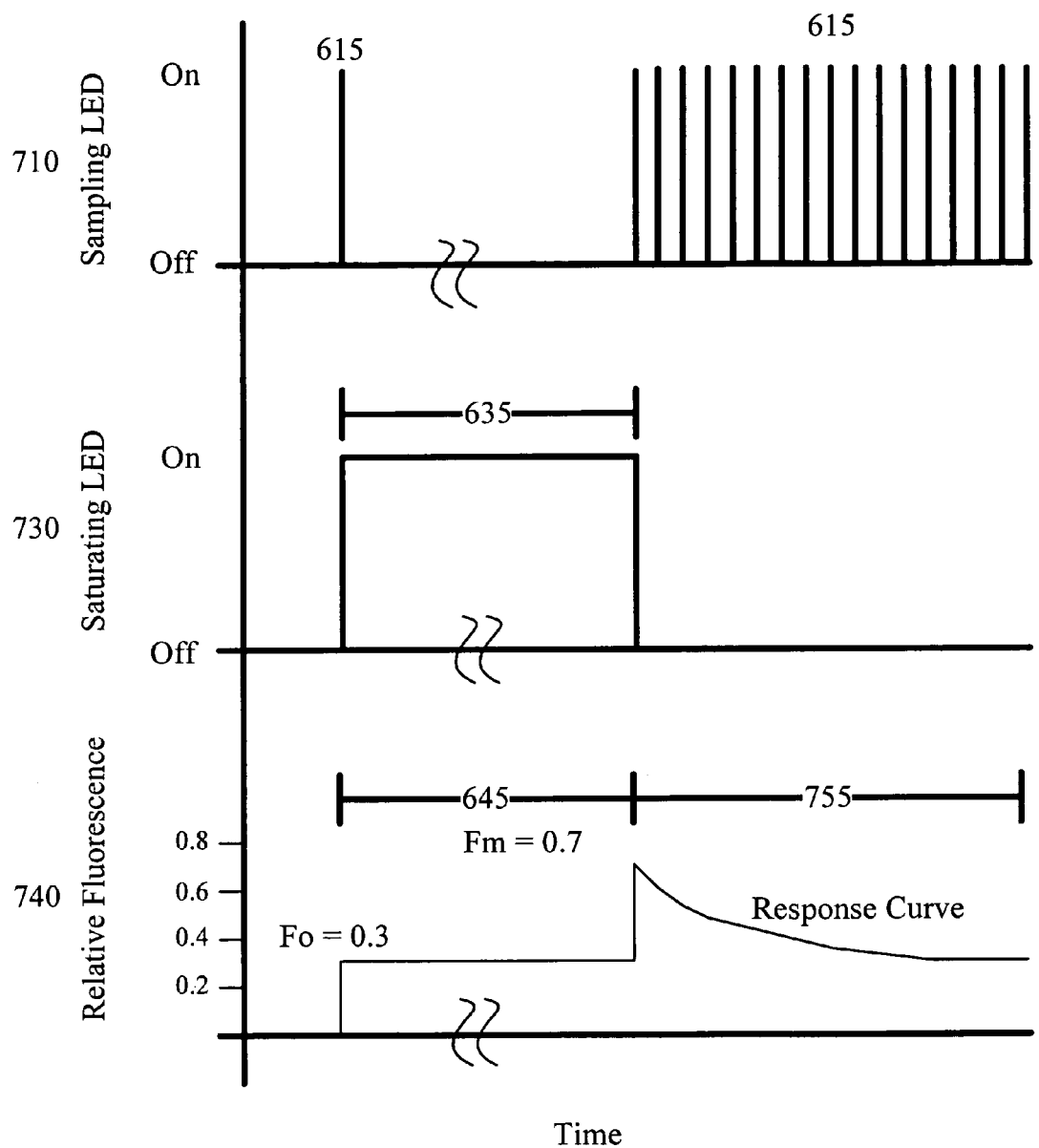
FIG. 7 illustrates another protocol for the fluorometer to determine certain parameters of the photosynthetic process.
Figure 8:
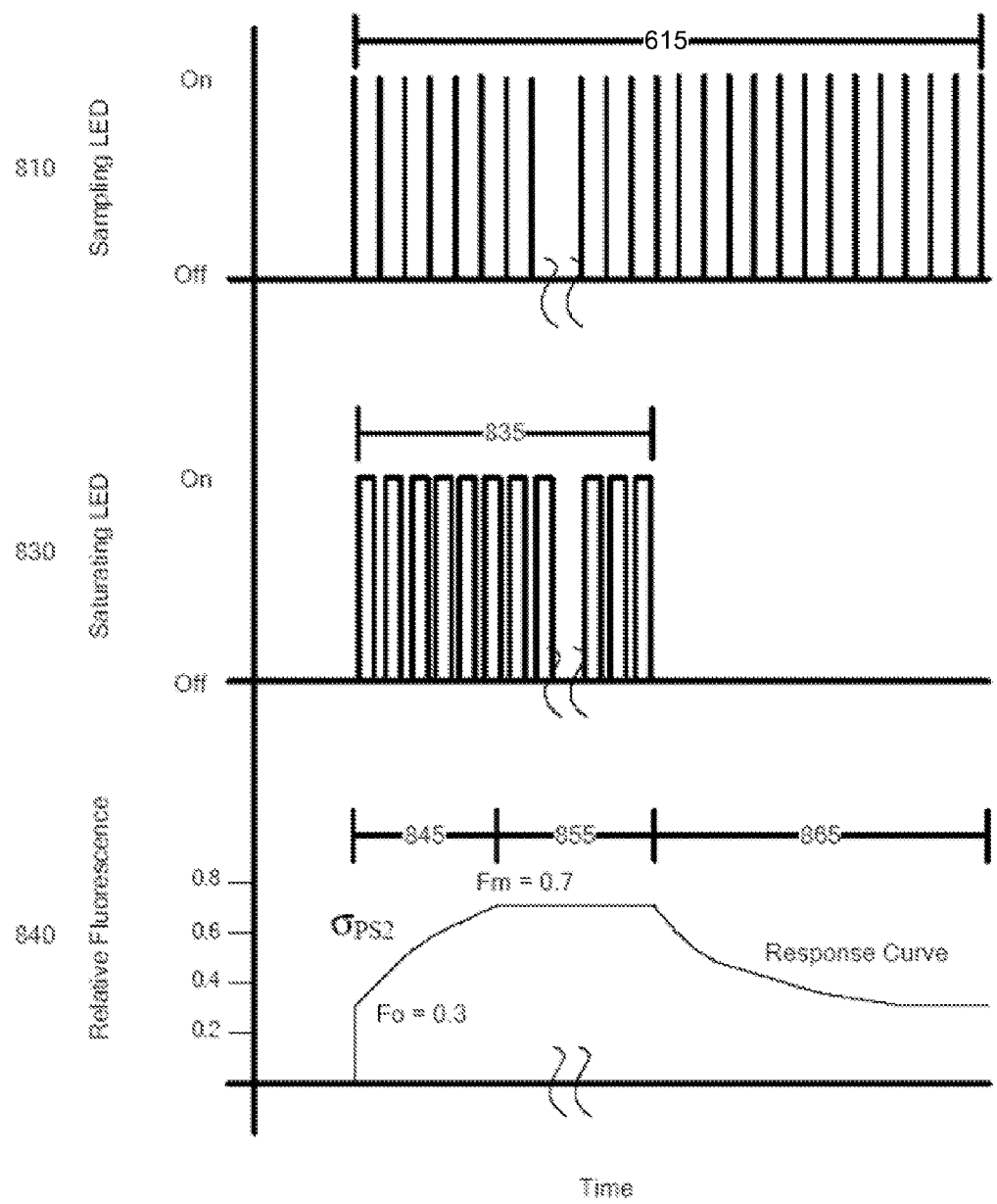
FIG. 8 illustrates yet another protocol for the fluorometer to determine certain parameters of the photosynthetic process.

The invention can be used to determine multiple parameters of the photosynthetic process. FIGS. 6 through 8 illustrate different protocols that can be used to determine an increasing number of parameters.

FIG. 6 illustrates a protocol that determines the yield of the photosynthetic process. This protocol involves dark adapting the sample as described above and taking one fluorescent measurement to measure Fo, using the sampling LED 110 to illuminate the sample, to obtain a minimum fluorescent value. The illumination by the sampling LED 110 causes the sample to fluoresce, the detection circuitry 290 then detects this fluorescence. Then the saturating LED 130 is turned on for some period of time (typically 1 second), and taking a second measurement immediately after saturating LED 130 turns off to measure Fm. Variable fluorescence (Fv) is determined by subtracting Fo from Fm. Yield is determined by dividing Fv by Fm, giving a number between 0 and 1.

As shown in the figure, graph 610 of sampling LED 110 shows the "on" or "off" state of the sampling LED 110 (not shown in FIG. 6) versus time. The spikes 615 represent the sampling LED 110 being turned on for a brief time and then turned off for a longer period of time.

Graph 630 of saturating LED 130 shows that saturating LED 130 has an "on" period 635 ending just before the sampling LED 110 turns on for the second time. Graph 640 represents the relative fluorescence versus time. Section 645 represents the relative fluorescence while the saturating LED 130 is on. Section 655 represents the relative fluorescence just after the saturating LED 130 has been turned off and the sampling LED 110 has flashed.

FIG. 7 illustrates a protocol that measures the response curve of the sample. The protocol starts by duplicating the protocol of FIG. 6. However, in this protocol, measurements continue to be made after Fm has been measured. The measurements continue until the sample's fluorescent output diminishes back to its Fo value. The resulting response curve is another measure of the photosynthetic process. It is the prime measurement used in an instrument to protect natural water supplies against chemical or biological hazards as described by Miguel Rodriguez, Jr. et. al. in the article *Sensors For Rapid Monitoring Of Primary-Source Drinking Water Using Naturally Occurring Photosynthesis* published in the Spring 2002 edition of the journal *Biosensors and Bioelectronics*.

As shown in the figure, graph 710 of sampling LED 110 shows the "on" or "off" state of the sampling LED 110 (not shown in FIG. 7) versus time. The spikes 615 represent the sampling LED 110 being turned on for a brief time and then turned off for a longer period of time. Note that in FIG. 7 there are many spikes 615 after the Saturating LED 130 has been turned off.

The graph 730 of saturating LED 130 shows that saturating LED 130 has an "on" period 635 ending just before the sampling LED 110 turns on for the second time. Graph 740 represents the Relative Fluorescence versus time. Section 645 represents the relative fluorescence while the saturating LED 130 is on. Section 755 represents the relative fluorescence just after the saturating LED 130 has been turned off and the Sampling LED 110 begins flashing repeatedly.

FIG. 8 illustrates another protocol that determines the functional absorption cross-section of PS2 ($\sigma_{PS2}$). In this protocol saturating LED 130 is pulsed instead of left on continuously. During the period of time when saturating LED 130 is off a measurement is made. This allows a curve to be generated of the fluorescent response of the sample as it is being saturated. Measuring the initial slope of this response gives a measurement of $\sigma_{PS2}$. This method can be refined by varying the pulse duration of the saturating pulses as well as the pulse intensity.

By varying the combination of saturating pulse duration and intensity and sampling times, many protocols can be developed to measure additional parameters of the photosynthetic process. Examples of additional protocols can be found in Kolber III with further protocols likely to be developed as knowledge in the field expands.

As shown in the figure, graph 810 of sampling LED 110 shows the "on" or "off" state of the sampling LED 110 (not shown in FIG. 8) versus time. The spikes 615 represent the sampling LED 110 being turned on for a brief time and then turned off for a longer period of time. Note that in FIG. 8 the spikes 615 are closer together than in FIG. 6, after the Saturating LED 130 has been turned off.

The graph 830 of saturating LED 130 shows that saturating LED 130 has several "on" periods 835 ending just before the sampling LED 110 turns on each time. Graph 840 represents the Relative Fluorescence versus time. Section 845 represents the relative fluorescence while the saturating LED 130 is on and before the sample is saturated. Section 855 represents the relative fluorescence while the saturating LED 130 is on and after the sample is saturated. Section 865 represents the relative fluorescence just after the saturating LED 130 has been turned off and the Sampling LED 110 continues to flash repeatedly.

As mentioned previously, in the description of FIG. 5, some embodiments use a photodiode 170 that has a high enough dynamic range to distinguish between ambient light, fluorescence caused by saturating LED 130, and fluorescence caused by sampling LED 110. These embodiments allow measurements to be made, using the sampling LED, while the saturating LED stays on. In such embodiments the graph 830 would look like the graph 630 from FIG. 6.

V. Alternative Embodiments

Figure 9:
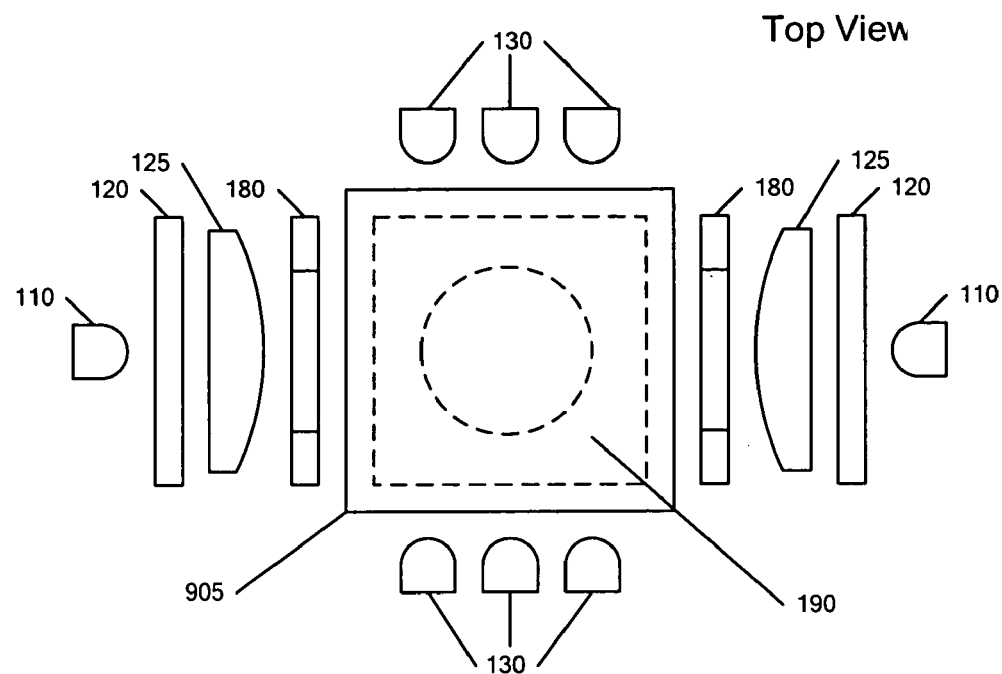
FIG. 9 illustrates an alternative embodiment of the fluorometer.
Figure 9:
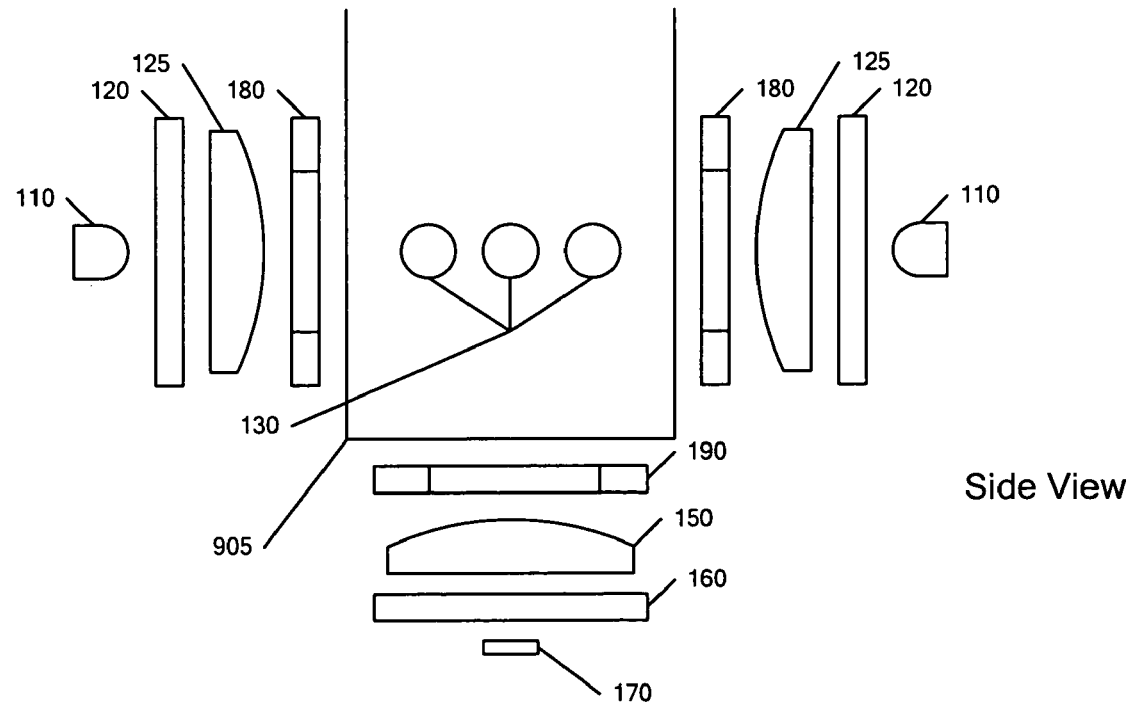

FIG. 9 illustrates an alternative embodiment of the invention. As shown in this figure, the sample container is a cuvette 905 that is square. However, in other embodiments, the cuvette 905 can be round. In some embodiments, the cuvette 905 is made of glass or plastic. As further shown in this figure, the photodetector 170 and its associated optical components (e.g., optical components 150, 160, and 190) are placed on the bottom of cuvette 905 facing up to detect the emitted light. In some embodiments, two sampling LEDs 110 and their associated optical components (e.g., optical components 120, 125, and 180), shine light into the side of the cuvette 905. In other embodiments, there can be more or fewer than two sampling LEDs 110.

FIG. 9 further shows six saturating LEDs 130 that are placed on the remaining sides of cuvette 905. In some embodiments, there can be more or fewer than six saturating LEDs 130. In some embodiments, this configuration of the saturating LEDs 130 provides the advantage of placing several LEDs around the sample while keeping them all orthogonal to the photodetector 170.

Figure 10:
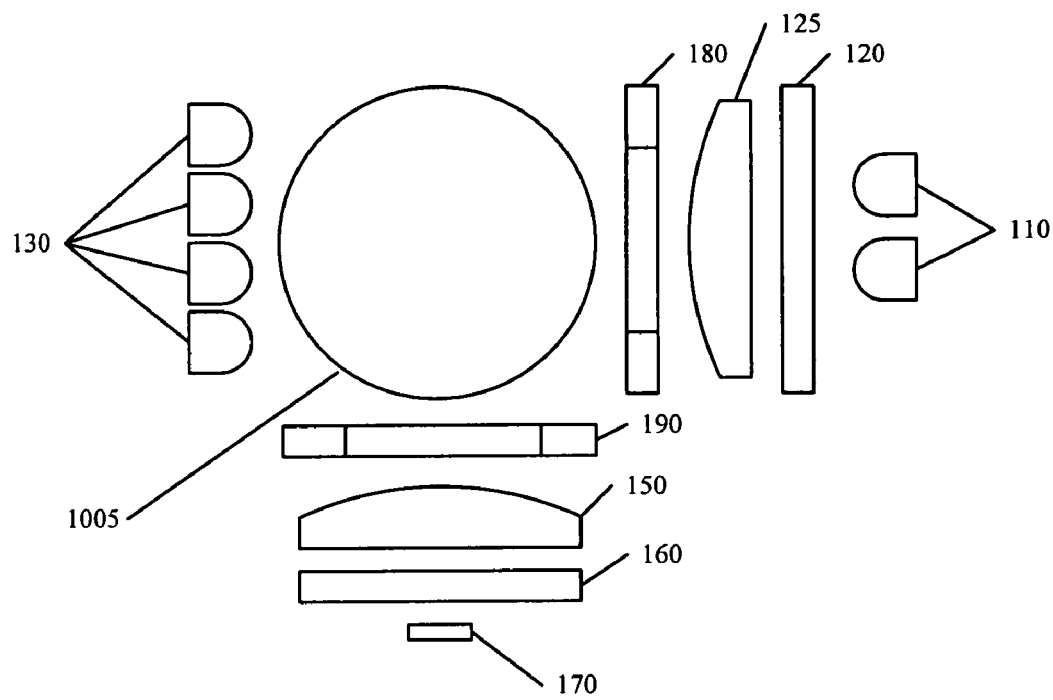
FIG. 10 illustrates another alternative embodiment of the fluorometer.
Figure 10:
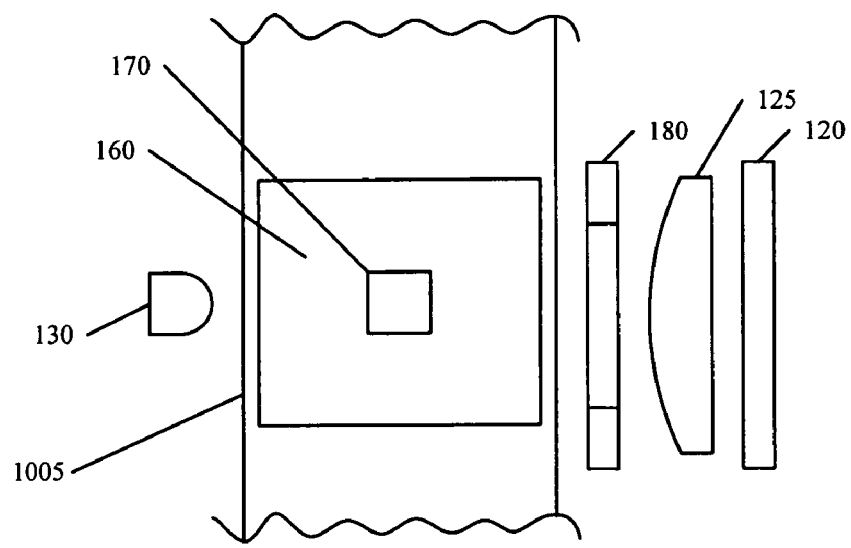

FIG. 10 illustrates another alternative embodiment for an application where the sample container is a round flowcell 1005. In some embodiments, a liquid flows through the round flowcell 1005. As shown in this figure, the photodetector 170 and its associated optical components (e.g. optical components 150, 160, and 190) are placed on a side of the flowcell 1005. Furthermore, the two sampling LEDs 110 and their associated optical components (e.g., optical components 120, 125, and 180) shine light into the side of the flowcell 605 that is orthogonal to the photodetector 170. In some embodiments, there can be more or fewer than two sampling LEDs 110. FIG. 10 further shows four saturating LEDs 130 that are placed opposite to the sampling LEDs 110. In some embodiments, there can be more or fewer than four saturating LEDs 130.

In some embodiments, using more saturating LEDs 130 may be required if the sample container 105, cuvette 505, or flowcell 1005 has a large volume that holds a large sample size, which requires more light to accurately measure the fluorescent response of the sample.

Figure 11:
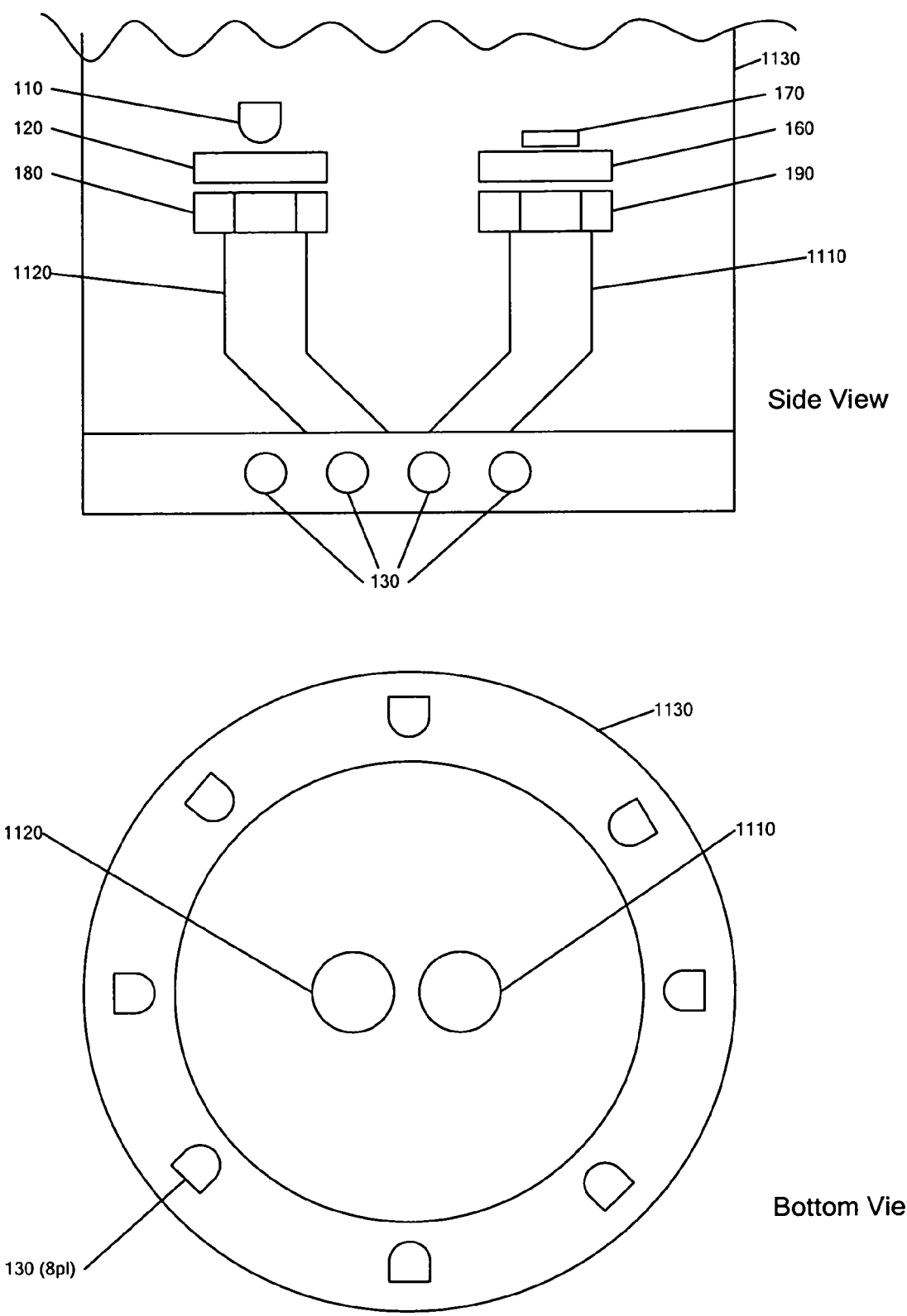
FIG. 11 illustrates another alternative embodiment of the fluorometer.

FIG. 11 illustrates yet another alternative embodiment for an application where the invention is housed in watertight container 1130. In some embodiments, the watertight container 1130 is used in submersible applications. As shown in this figure, an optical fiber 1120 is used to carry light from the sampling LED 110 to the ambient liquid. Similarly, an optical fiber 1110 carries the resulting emission light from the ambient liquid to the photodetector 170. As further shown in this figure, several saturating LEDs 130 (in this illustration 8) are placed in a ring around the ambient liquid at the end of optical fibers 1110 and 1120. In some embodiments, there can be more or fewer than 8 saturating LEDs 130.

Figure 12:
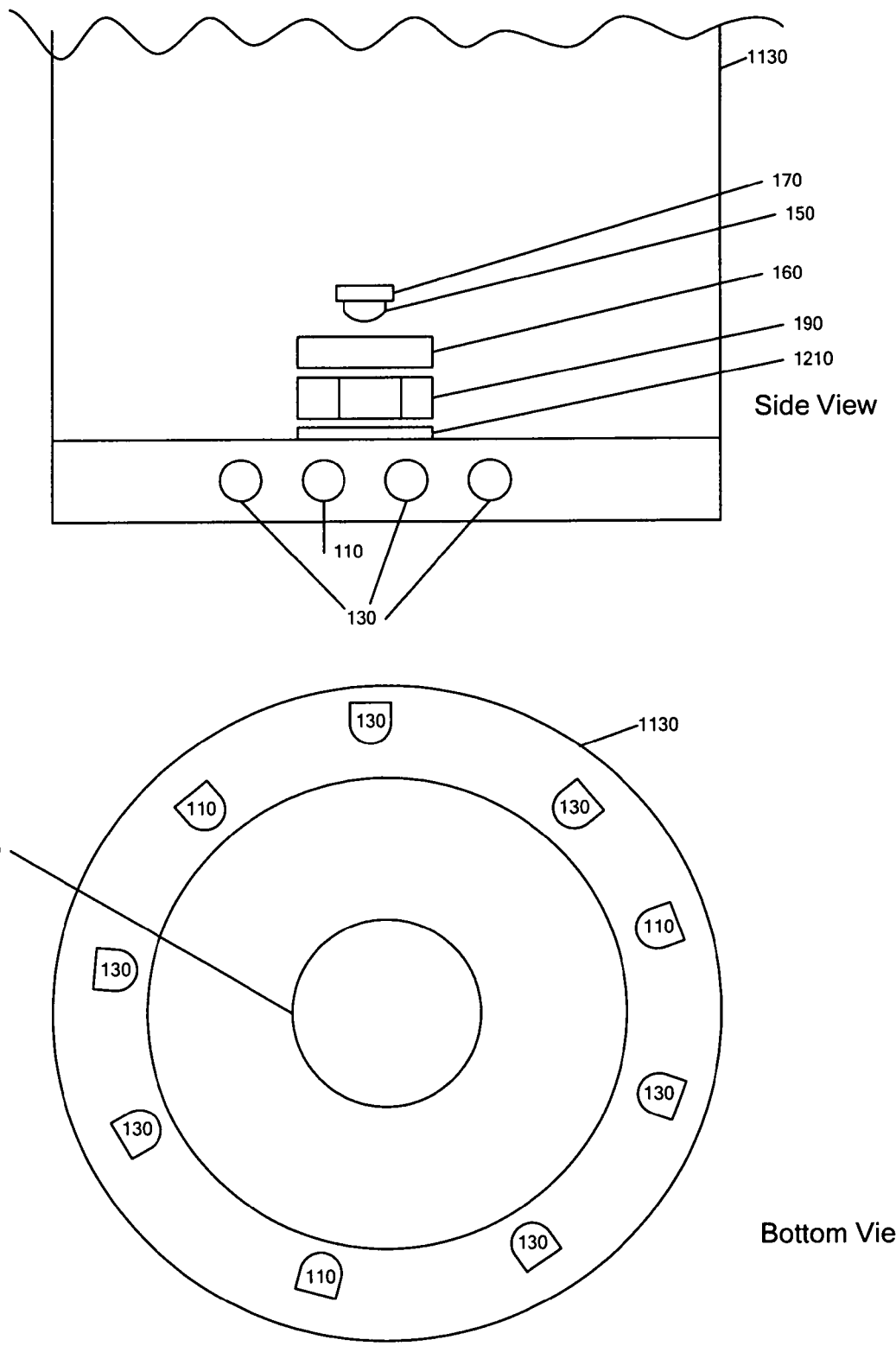
FIG. 12 illustrates another alternative embodiment of the fluorometer.

FIG. 12 illustrates another alternative embodiment for an application where the invention is housed in watertight container 1130. This embodiment is different from the embodiment illustrated in FIG. 11. As shown in FIG. 12, both the sampling LEDs 110 and the saturating LEDs 130 are arranged in the same plane. The detection optics, including an aperture 190, an emission filter 160, a lens 150 and photodiode 170, are separated from the water by a window 1210. As further shown in this figure, several saturating LEDs 130 (here 6) are placed, along with several sampling LEDs (here 3) in a ring around the ambient liquid outside the window 1210. In some embodiments, there can be more or fewer than 6 saturating LEDs 130 and/or more or fewer than 3 sampling LEDs 110.

Some embodiments, including some submersible embodiments, use very little power. In some cases the maximum power consumption of the fluorometer may be 10 watts, 5 watts, 2.5 watts, or even 1 watt. Generally, the maximum power consumption occurs when the saturation LED 130 is on. When the saturation LED is off, the power consumption of some embodiments drops below 1 watt.

While the invention has been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

What is claimed is:

1. An active fluorometer for measuring a fluorescence of a photosynthetic material in a liquid, the active fluorometer comprising:
   a) a set of sampling light emitting diodes for supplying a sampling excitation light to direct towards the liquid;
   b) a set of saturating light emitting diodes for supplying a saturating excitation light to direct towards the liquid; and
   c) a photodiode for measuring a detected light emitted from the liquid in response to said sampling excitation light, said detected light used for measuring said fluorescence of said photosynthetic material in the liquid.

2. The active fluorometer of claim 1, wherein the set of sampling light emitting diodes includes only one light emitting diode.

3. The active fluorometer of claim 1, wherein the set of sampling light emitting diodes includes more than one light emitting diode.

4. The active fluorometer of claim 1, wherein the set of saturating light emitting diodes includes only one light emitting diode.

5. The active fluorometer of claim 1, wherein the set of saturating light emitting diodes includes more than one light emitting diode.

6. The active fluorometer of claim 1, wherein the photodiode is connected to an electrical amplifier.

7. The active fluorometer of claim 6, wherein an output of the electrical amplifier is sent to a first holding circuit when said set of sampling light emitting diodes is on.

8. The active fluorometer of claim 7, wherein the output of the electrical amplifier is sent to a second holding circuit when said set of sampling light emitting diodes is off.

9. The active fluorometer of claim 8, wherein an output of the first holding circuit is compared to an output of the second holding circuit.

10. The active fluorometer of claim 6, further comprising a control circuit for controlling at least one component from a set of components comprising a diode of said set of sampling light emitting diodes, a diode of said set of saturating light emitting diodes, and a switch that determines whether a first holding circuit receives an output of the electrical amplifier.

11. The active fluorometer of claim 1, further comprising an optical fiber to carry said sampling excitation light from said set of sampling light emitting diodes to the liquid.

12. The active fluorometer of claim 1, wherein the liquid is contained in a container.

13. The active fluorometer of claim 1, wherein at least one diode of said set of saturating light emitting diodes is orthogonal to the photodiode.

14. The active fluorometer of claim 1, wherein at least one diode of said set of sampling light emitting diodes is orthogonal to the photodiode.

15. An active fluorometer for measuring a fluorescence of a sample, the fluorometer comprising:
   a) a sampling light source for supplying excitation light to direct to the sample,
   b) a saturating light source for supplying saturating excitation light to the sample; and
   c) a photodetector for measuring light emissions from the sample,
   d) wherein the fluorometer uses no more than 10 watts at maximum power consumption.

16. The active fluorometer of claim 15, wherein the fluorometer uses no more than 5 watts at maximum power.

17. The active fluorometer of claim 16, wherein the fluorometer uses no more than 2.5 watts at maximum power.

18. The active fluorometer of claim 15, wherein the fluorometer uses no more than 1 watt at maximum power.

19. The active fluorometer of claim 15, wherein the fluorometer uses less than 0.5 watts when the saturating light source is off.

20. A method for measuring active fluorescence in liquid samples, the method comprising
   a) lighting a liquid sample with a first light emitting diode;
   b) saturating a liquid sample with a second light emitting diode; and
   c) measuring the fluorescence of the liquid sample;
   d) recording a measurement of the fluorescence.

21. The method of claim 20, wherein the first light emitting diode is a sampling light emitting diode.

22. The method of claim 21, wherein the second light emitting diode is a saturating light emitting diode.

* * * * *